United States Patent [19]

Shoji et al.

[11] Patent Number: 4,586,933
[45] Date of Patent: May 6, 1986

[54] DUAL ARTICULATING TOTAL KNEE PROSTHESIS

[76] Inventors: Hiromu Shoji, 14 Grand Canyon Dr., New Orleans, La. 70014; Shin'ichi Yoshino, 2-35-14, Asahi-machi, Nerima-ku, Tokyo, Japan

[21] Appl. No.: 644,674

[22] Filed: Aug. 27, 1984

[30] Foreign Application Priority Data

Sep. 30, 1983 [JP] Japan .................. 58-182908

[51] Int. Cl.$^4$ .............................................. A61F 1/00
[52] U.S. Cl. .................................... 623/20; 128/92 C
[58] Field of Search ................... 3/1.9, 1.91, 1.911; 128/92 C

[56] References Cited

U.S. PATENT DOCUMENTS

| 4,081,866 | 4/1978 | Upshaw et al. | 3/1.911 |
| 4,085,466 | 4/1978 | Goodfellow et al. | 3/1.911 |
| 4,209,861 | 7/1980 | Walker et al. | 3/1.911 |
| 4,340,978 | 7/1982 | Buechel et al. | 3/1.911 |

Primary Examiner—Richard J. Apley
Assistant Examiner—David J. Isabella
Attorney, Agent, or Firm—Wenderoth, Lind & Ponack

[57] ABSTRACT

A dual articulating total knee prosthesis comprises a femoral component, a tibial tray, and a plurality of movable inserts. The femoral component has a medial condyle, a lateral condyle, and a near anatomical curvature at a first articulating surface. The movable inserts are arranged between the femoral component and the tibial tray. These inserts provide the first articulating surface at an upper surface of the inserts in contact with the medial and lateral condyles of the femoral component. The inserts also provide the second articulating surface at a lower surface of the inserts in contact with the track of the tibial tray.

The prosthesis is able to perform near full flexion without dislocation of the inserts and with a near physiological knee motion pattern. Stress concentration at the articulating surface is also avoided.

6 Claims, 11 Drawing Figures

DUAL ARTICULATING TOTAL KNEE PROSTHESIS

BACKGROUND OF THE INVENTION

1. Field of the Invention

This invention pertains to a total knee prosthesis.

2. Description of the Prior Art

The articular surface of the knee joint is liable to sustain damage due to trauma, arthritis, and other diseases. In the event that the extent of the damage is such that the function of the knee is irrestorable without surgery, total knee replacement is one of the surgical procedures employed in which the damaged articular surface is resected and a total knee prosthesis is implanted. The Oxford-type total knee prosthesis is one of these prostheses. This prosthesis is an excellent device but there is a limit in flexion capacity and an occasional dislocation of the inserter, particularly at more than 90° of flexion.

New Jersey Meniscal Bearing Knee Replacement is one of the improved modifications of the Oxford-type prosthesis. In this prosthesis, the articulating surface of the femoral prosthesis is made of three different radii in shape, and stems are provided for its fixation. The bottom surface of the inserter has a projecting dovetail which glides in the corresponding groove of the tibial tray. The drawback of this system is that stress associated with knee motion can cause a breakage or cold flow of the projecting dovetail and/or its excessive wear, the particles from which can be harmful to the human body.

SUMMARY OF THE INVENTION

The total knee prosthesis of the present invention includes a femoral component with near anatomical curvature, movable inserts with concave articulating surfaces at the top and bottom, and a tibial tray with convex tracks and posterior stops. The present invention has a capability of performing near full flexion without insert dislocation and a near physiological knee motion pattern. Stress concentration at the articulating surfaces is avoided so that cold flow, excess wear, or breakage of the insert is less likely to occur. The geometry of the articulating surfaces and posterior stops has made dislocation of the insert extremely difficult.

DETAILED DESCRIPTION OF THE PREFERRED EMBODIMENTS

Figure 1:
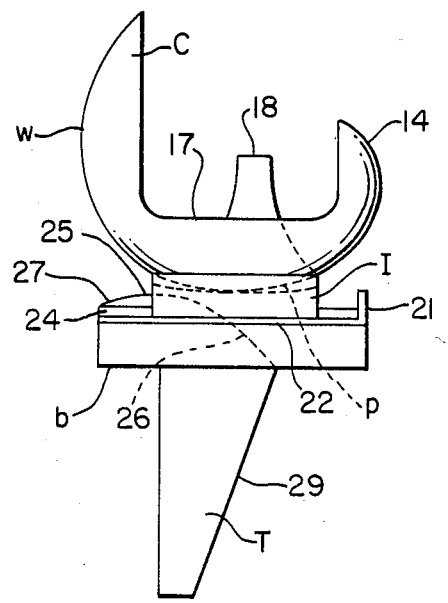
FIG. 1 is a lateral view of the dual-articulating total knee prosthesis in one embodiment.
Figure 2:
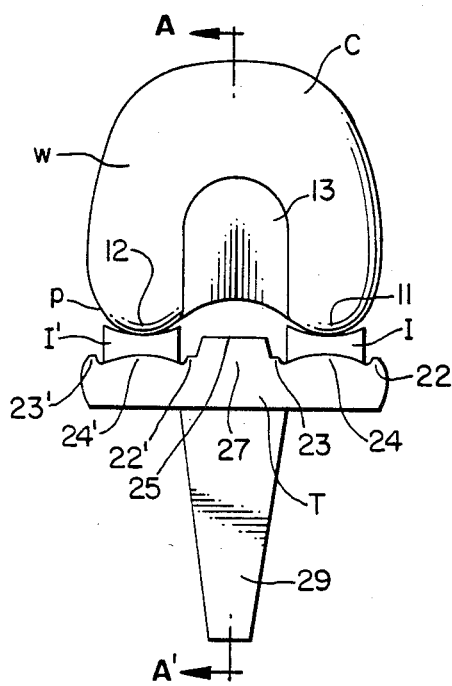
FIG. 2 is a frontal view of the total knee prosthesis shown in FIG. 1.
Figure 3:
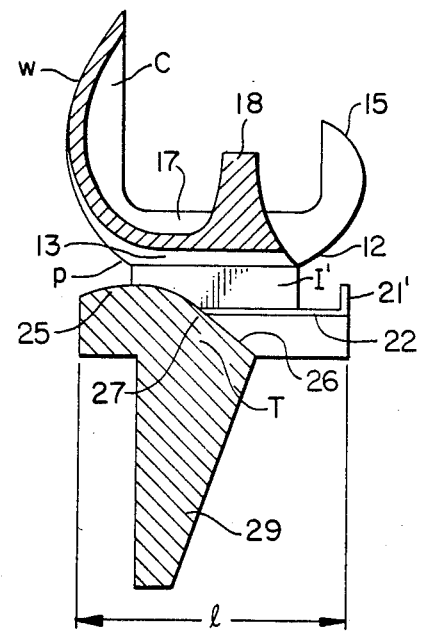
FIG. 3 is a cross-sectional view of FIG. 2 taken along line A—A'.
Figure 4:
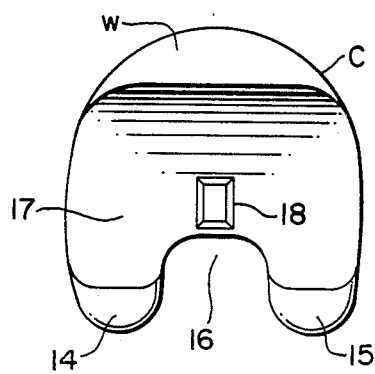
FIG. 4 is a top view of the femoral component of the total knee prosthesis.
Figure 6:
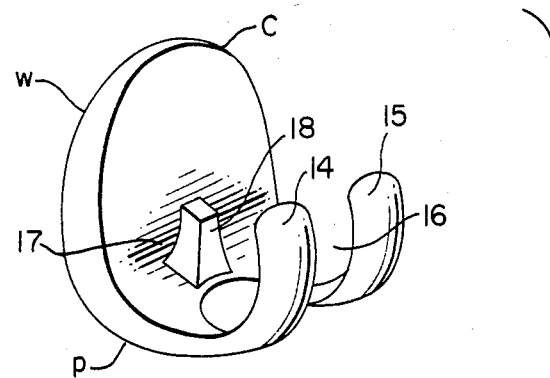
FIG. 6 is an exploded isometric view of the components of the total knee prosthesis.
Figure 6:
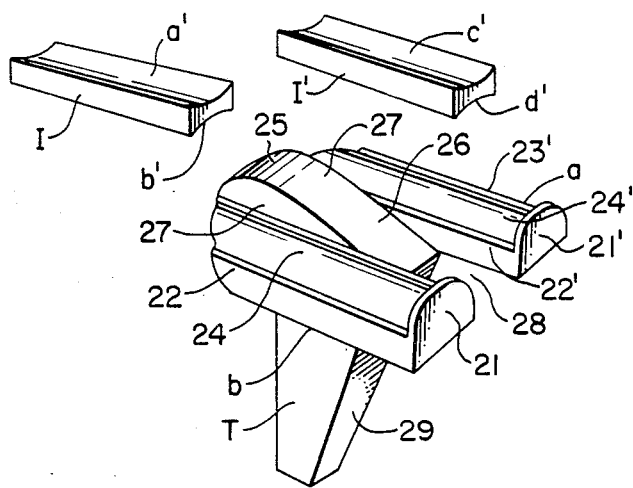

In FIG. 1 there is shown a first embodiment of the total knee prosthesis of the present invention comprising a femoral (thigh) component C, a movable insert I, and a tibial (shin) tray T. In FIG. 2, an articulating surface p is shown between a medial femoral condyle or knuckle 11, a lateral femoral condyle or knuckle 12, and upper surfaces of movable inserts I and I'. An intercondylar groove 13 of the femoral component C is shown only in FIG. 2 while an anterior flange w of the femoral component C is shown in both FIGS. 1 and 2. In FIG. 4, there are shown a space 16 between posterior femoral condyles 14 and 15 and a stem 18 at the bottom of a valley 17 partially surrounded by the anterior flange w of the femoral component C. In the exploded isometric view of FIG. 6, there are shown a top surface a and a bottom surface b of the tibial tray T. Also, there are shown upper surfaces a' and c' and lower surfaces b' and d' of the movable inserts I and I', respectively. In FIG. 3, it may be seen that a dimension "l" indicates an anteroposterior length of the top surface a of the tibial tray T. As best seen in FIG. 6, stops 21 and 21' are arranged at one end of the tibial tray T for stopping movement of the movable inserts I and I'. Side moldings 22, 22' and 23, 23' are provided along convex tracks 24 and 24'. An anterior elevation 25 is located at one end of a central bulging track 27 having a posterior slope 26. A space 28 is left between the posterior slope 26 of the central bulging track 27 and the convex tracks 24, 24'. The tibial tray T has a peg 29 for insertion into the tibial bone of the shin or lower leg.

FIGS. 7–11 illustrate a second embodiment of the total knee prosthesis of the present invention. The same reference numbers used in describing elements of the first embodiment illustrated in FIGS. 1–6 are used in describing identical elements of the second embodiment. However, additional elements in the second embodiment not in the first embodiment include a second stem 18', best shown in FIG. 10, and a second peg 29', best shown in FIG. 8.

The dual articulating prosthesis of the present invention comprises the femoral component C, two movable inserts I, I', and the tibial tray T. The prosthesis is primarily used for the knee with intact posterior cruciate ligaments, although it can be used in cruciate sacrificing form too. The femoral component C and the tibial tray T are manufactured with mechanically strong, corrosion-resistant, and biocompatible metallic materials, (i.e. Co—Cr alloy, stainless-steel, titanium alloy, etc.) in either casting or wrought fashion. Inserts I, I' are made of high density polyethylene or its derivatives.

Figure 7:
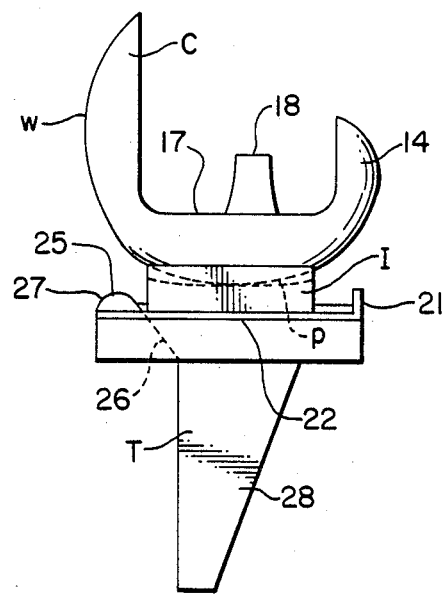
FIG. 7 is a lateral view of the dual articulating total knee prosthesis in another embodiment.
Figure 9:
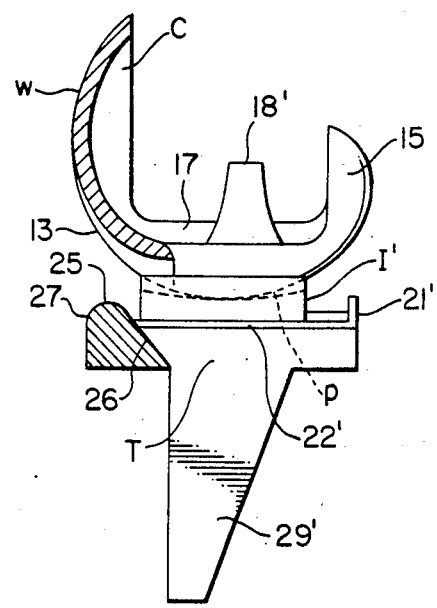
FIG. 9 is a cross-sectional view of FIG. 8 taken along line B—B'.
Figure 10:
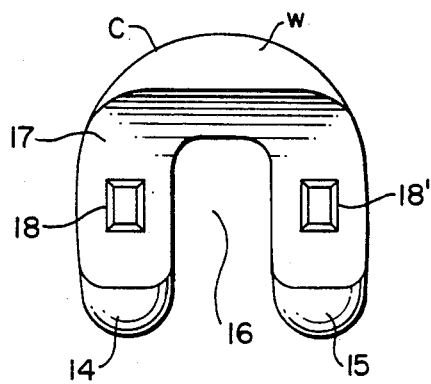
FIG. 10 is a top view of the femoral prosthesis of the second embodiment.

As shown in FIG. 1, the femoral component C has the following features: The highest point of the anterior flange w is taller than that of the posterior condyles 14 and 15. As shown in FIG. 2, the area posterior to the intercondylar groove 13 is void of metal. As shown in FIG. 3, the articulating surface p of the anterior flange w is mildly curved, but the inner cut surface is flat and almost vertical to the horizon. The medial condyle 11 and the lateral condyle 12 both have a convex appearance in the frontal view of FIG. 2 and the intercondylar groove 13 is formed between them. The articulating surface p of the femoral component C has a near anatomical shape. As shown in FIGS. 2-4, the medial condyle 11 and the lateral condyle 12 extend posteriorly to form posterior condyles 14, 15, the inner cut surface of which stands vertical to the horizon. As shown in FIG. 4, between posterior condyles 14, 15, a space 16 exists. The bottom of the valley 17, surrounded by anterior flange w, the articulating surface p, and the posterior condyles 14, 15, contains at least one stem 18. In FIG. 2, the intercondylar groove 13 extends into the middle of the anterior flange w in order to accommodate a patella (kneecap) prosthesis. The space 16 of FIG. 4 is provided to accommodate cruciate ligaments. In the situation where only a posterior cruciate ligament is to be spared, the anteroposterior dimension of the space 16 is approximately ⅓ of that of the femoral component C, as shown in FIGS. 1, 3, 4, and 6. In the event that both anterior and posterior cruciate ligaments are to be spared, the anteroposterior dimension of the space 16 is extended to approximately ⅔ of that of the femoral component C at the sacrifice of a portion of the intercondylar groove 13, as shown in FIGS. 7, 9, and 10. The stem 18 of FIG. 4 has a rectangular pillar shape and at least one stem is arranged at the bottom of the valley 17. The stem 18 is fixed to the cut surface of the femur (thigh) in the routine surgical manner. When the space 26 is relatively small so as to have to accommodate only the posterior cruciate ligament alone, one stem 18 arranged at the bottom of the valley 17 close to the space 16 is sufficient, as shown in FIGS. 3, 4, and 6. When the space 16 is relatively large in order to accommodate both anterior and posterior cruciate ligaments, two stems 18, 18' are used at the bottom of the valley 17 where the space 16 is sandwiched, as shown in the second embodiment of FIGS. 9 and 10. The stems 18, 18' have a tapered rectangular pillar shape so that is makes stress dissipate to the femur and has a good resistance to rotational stress.

Figure 5:
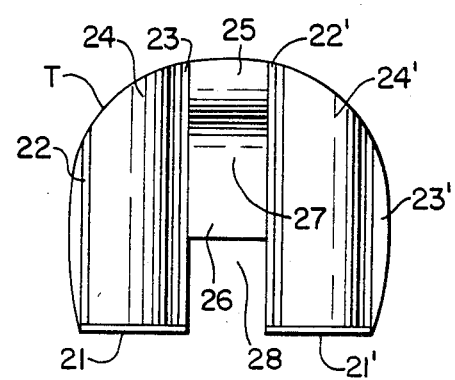
FIG. 5 is a view of the tibial tray of the total knee prosthesis.

As shown in FIG. 5, the tibial tray T has an appearance of a U-shaped disc, containing three bulging tracks placed parallel to each other. Two of the bulging tracks 24, 24' located at both sides of the top a of the tray T, are termed convex tracks which articulate with the inserts I, I' of FIG. 6. The other bulging track 27, located centrally between the two convex tracks 24, 24', is elevated anteriorly, slopes down posteriorly, and does not form an articulating surface. At the end of the posterior slope 26 in this central bulging track 27, a rectangular space 28 is formed and surrounded by this end of the slope 26 and by the two convex tracks 24, 24'. The bottom of the tibial tray T contains at least one peg 29. The convex tracks 24, 24' are provided with stops 21, 21' at their posterior edges. These stops 21, 21' have an appearance of arcades. Both sides of the convex tracks 24, 24' can be surrounded by side moldings 22, 23, 22', 23', as needed. The anterior edge of the convex tracks 24, 24' can be slightly enlarged, as necessary.

The stops 21, 21' are structured just enough to prevent posterior displacement or dislocation of the inserts I, I', and their shape can be a simple protuberance or chair-back type as shown in FIGS. 1, 3, 5, 6, 7, 9, and 11. As shown in FIG. 6, the posterior stops 21, 21', the side moldings 22, 23, 22', 23', and the slight enlargement at the anterior edge of the convex tracks 24, 24', on top of the concavity feature of the inserts a', b', c', d', provide additional factors to prevent displacement or dislocation of the inserts I, I'. Such dislocation could otherwise possibly occur due to excessive movement of the inserts caused by stress from knee motion.

Figure 8:
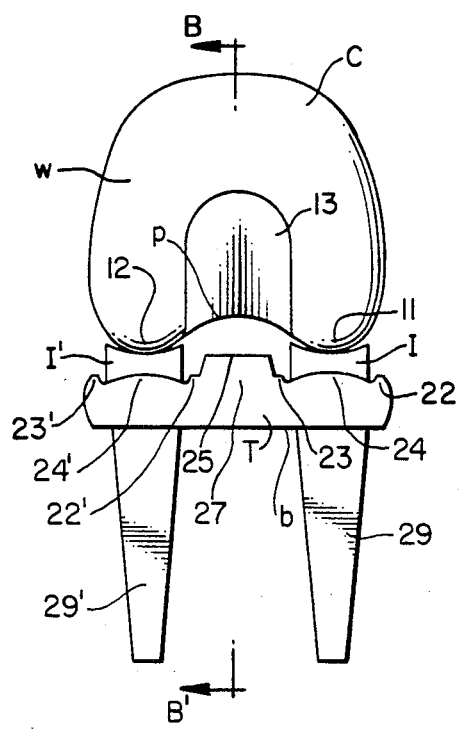
FIG. 8 is a frontal view of the second embodiment shown in FIG. 7.
Figure 11:
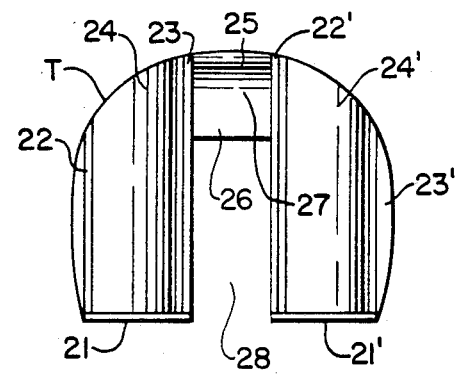
FIG. 11 is a top view of the tibial tray of the second embodiment.

As shown in FIG. 6, the central bulging track 27 has an anterior elevation 25 which gradually transforms to the posterior slope 26. The posterior slope 26 intersects with the bottom of the tibial tray T at approximately 45°. The posterior slope 26 with its edge and the convex tracks 24, 24' form the space 28, which is created to accommodate cruciate ligaments. In the situation where only the posterior cruciate ligament is to be spared, the anteroposterior dimension of the space 28 is approximately ⅓ of that of the tibial tray T, as shown in FIGS. 1, 3, 5, and 6. In the event that both anterior and posterior cruciate ligaments are to be spared, the anteroposterior dimension of the space 28 is approximately ⅔ of that of the tibial tray T, as shown in FIGS. 7, 9, and 11. In FIG. 6, the peg 29 has a tapered, rectangular pillar shape and at least one peg is attached to the bottom of the tibial tray T which is to be fixed to the cut surface of the tibia (shinbone) in the routine surgical manner. When the space 28 is relatively small so as to have to accommodate only the posterior cruciate ligament alone, one peg 24 attached directly below the posterior slope 26 is sufficient, as shown in FIGS. 2, 3, 5, and 6. When the space 28 is relatively large in order to accommodate both anterior and posterior cruciate ligaments, two pegs 29, 29' are attached directly below the convex tracks 24, 24' at the bottom surface of the tibial tray T, as shown in FIGS. 8, 9, and 11. The peg 29 has a tapered, rectangular pillar shape so that it makes stresses dissipate to the tibia (shinbone) and has a good resistance against rotational stress.

Each of the inserts I, I' has an appearance of a kind of rectangular board, the cross section of which has a shape of a concave lens, as shown in FIGS. 1, 2, 3, 6, 7, 8, and 9. As shown in FIG. 6, certain areas of the inserts I, I' form concave surfaces to articulate with the femoral component C and the tibial tray T. The concavity of the upper surfaces a' and c' of the inserts I and I', respectively, is of lesser degree than that of the lower surfaces b' and d' in the frontal view. In the lateral view, the upper surfaces a' and c' adopt the concave curvature of the same or a slightly larger radius as that of the femoral condyles 11, 12 to articulate against the femoral component C. The degree of concavity of the lower surfaces b', d' in the frontal view of approximately the same as that of convex track 24, 24' of the tibial tray T. The lateral view of the lower surfaces b', d' presents a flat appearance. The anteroposterior dimension of the inserts I, I' is approximately 60% to 90% of that length "l" of the tibial tray T. As shown in FIG. 2, the inserts I, I' are placed between the femoral condyles 11, 12 of the femoral component C and convex tracks 24, 24' of the tibial tray T, to function as a sort of menisci, i.e. fibrous cartilage within a joint of the knee.

The knee motion presents very complex kinematics which involves a combination of sliding, rolling, and axial rotation of the femur (thighbone) on the tibia (shinbone). Active extension of the knee causes external rotation of the tibia on the femur and active flexion does the reverse. As shown in FIG. 6, when the convexity of the upper surfaces a and c of the inserts I, I' is made with a larger radius than that of the femoral condyles 11, 12 of FIG. 2, a complex motion of the knee involved in flexion-extension is relatively unhindered. However, the drawback is that, in this situation, the inserts I, I' are more liable to dislocate than in a more constrained articulating relationship such as at the upper surfaces a', c' of insert I, I' of FIG. 6 and the femoral condyles 11, 12 of FIG. 6. Dislocation of the inserts I, I' occurs most frequently towards the posterior, followed by the sides. Anterior dislocation is least frequent. As shown in FIG. 6, the most common posterior dislocation is fully prevented by the presence of the stops 21, 21' provided at the posterior end of the convex tracks 24, 24' of the tibial tray T. Side dislocation is prevented by the near complete match in the concave-convex relationship between the lower surfaces b', d' of the inserts I, I' and the convex tracks 24, 24' of the tibial tray T. This dislocation preventive mechanism is further enhanced by the side moldings 22, 23, 22', 23', as needed. Anterior dislocation is prevented by enlarging the anterior edge of the convex tracks 24, 24' of the inserts I, I'.

Again referring to FIG. 6, when the anteroposterior and lateral configuration of the upper surfaces a', c' of the inserts I, I' is a perfect match against the configuration of the femoral condyle 11, 12, it makes dislocation of inserts I, I' more difficult, although complex kinematics in the knee motion may, to some extent, be affected.

The dual-articulating total knee prosthesis of the present invention provides excellent functioning as a total knee prosthesis by virtue of these features described thus far. To summarize its advantages:

(1) The articulation occurs in two places, namely at the femoral-insert and insert-tibial interfaces. Thus, stress concentration at the bone-prosthetic interfaces is reduced so that a chance of prosthesis fixation loosening after long term usage is lessened.

(2) The mobile feature of the inserts I, I40 makes it possible for the knee to follow the smooth, near normal kinematic pattern of motion. The increased contact area throughout the range of motion of the knee reduces the stress per area in the prosthesis, and thus reduces wear of the prosthetic component for the longevity of the implant.

(3) The dual-articulating features mentioned in (1) and the retainment of the cruciate ligaments make a far greater range of motion possible than conventional total knee prostheses have been able. The present invention can produce 140° flexion and even a squatting position becomes possible. Axial rotation does not occur in full extension and takes place only in flexion within the possible physiological extent.

(4) The near complete match in the concave-convex relationship between the lower surfaces b', d' of the inserts I, I' and the convex tracks 24, 24' of the tibial tray T, and the relationship between the upper surfaces a', c' of the inserts I, I' with the femoral condyles 14, 15, and the side moldings 22, 23, 22', 23' along the convex tracks 24, 24' of the tibial tray T, make it extremely difficult for the inserts I, I' to dislocate.

(5) The inserts I, I' of the ideal height are inserted horizontally almost in parallel to the cut surface of the tibial (shinbone) with the knee in 90° flexion, following the fixation of the femoral component C and the tibial tray T. This feature makes it more easy and reliable to restore complete stability of the knee both in extension and flexion than in a conventional total knee prosthesis, where some compromise has to be made in attempting a tight fitting of the components in a flexed position.

(6) The shape of the peg 29 of the tibial tray T and that of the stem 18 of the femoral component C are such that stresses dissipate relatively evenly to the bones and such shape resists axial rotary stress.

The two embodiments of the present invention described in the specification hereinabove are considered to be illustrative only since other modifications will be readily discerned by those skilled in the pertinent technology. In any event, the scope of the invention is intended to be covered by both the letter and the spirit of the claims appended hereto.

We claim:

1. A dual articulating total knee prosthesis, comprising;
    a femoral component having a medial condyle and a lateral condyle and also having a near anatomical curvature at a first articulating surface;
    a tibial tray having at least one track at a second articulating surface; and
    a plurality of movable insert means, arranged between the femoral component and the tibial tray, for providing the first articulating surface at an upper surface of the insert means in contact with medial and lateral condyles of the femoral component and for providing the second articulating surface at a lower surface of the insert means in contact with the track of the tibial tray;
    wherein said track of the tibial tray has an upper convex surface and includes, at its posterior end, a means for stopping movement of the movable insert means sliding thereon.

2. The dual articulating total knee prosthesis, according to claim 1, wherein:
    said femoral component includes a plurality of posterior femoral condyles and at least one stem means for fixing the femoral component to a cut surface of a femur bone.

3. The dual articulating total knee prosthesis, according to claim 1, wherein:
    said tibial tray includes a central bulging track having a posterior slope and an anterior elevation.

4. The dual articulating total knee prosthesis, according to claim 1, wherein:
    said track of the tibial tray has a shape of a rectangular box surrounded by side molding.

5. The dual articulating total knee prosthesis, according to claim 1, wherein:
    said tibial tray includes at least one peg means for fixing the tibial tray to a cut surface of a tibia bone.

6. The dual articulating total knee prosthesis, according to claim 1, wherein:
    each of the plurality of movable insert means has a shape of a rectangular box with its upper and lower surfaces being concave for matching with the medial and lateral condyles of the femoral component and for matching with the track of the tibial tray, respectively.

* * * * *